(12) United States Patent
Kim et al.

(10) Patent No.: US 11,554,158 B2
(45) Date of Patent: Jan. 17, 2023

(54) GPNMB COMPOSITIONS FOR TREATMENT OF SKIN WOUNDS

(71) Applicant: NORTHEAST OHIO MEDICAL UNIVERSITY, Rootstown, OH (US)

(72) Inventors: Min-Ho Kim, Hudson, OH (US); Fayez Safadi, Akron, OH (US); Bing Yu, Stow, OH (US)

(73) Assignees: NORTHEAST OHIO MEDICAL UNIVERSITY, Rootstown, OH (US); KENT STATE UNIVERSITY, Kent, OH (US)

( * ) Notice: Subject to any disclaimer, the term of this patent is extended or adjusted under 35 U.S.C. 154(b) by 168 days.

(21) Appl. No.: 16/093,270

(22) PCT Filed: Apr. 13, 2017

(86) PCT No.: PCT/US2017/027402
§ 371 (c)(1),
(2) Date: Oct. 12, 2018

(87) PCT Pub. No.: WO2017/180862
PCT Pub. Date: Oct. 19, 2017

(65) Prior Publication Data
US 2019/0134154 A1     May 9, 2019

Related U.S. Application Data

(60) Provisional application No. 62/321,919, filed on Apr. 13, 2016.

(51) Int. Cl.
*A61K 38/17* (2006.01)
*A61K 9/00* (2006.01)
*A61P 17/02* (2006.01)
*A61K 9/127* (2006.01)
*A61L 15/32* (2006.01)

(52) U.S. Cl.
CPC ........ *A61K 38/1709* (2013.01); *A61K 9/0014* (2013.01); *A61K 9/127* (2013.01); *A61L 15/325* (2013.01); *A61P 17/02* (2018.01); *A61L 2300/412* (2013.01)

(58) Field of Classification Search
None
See application file for complete search history.

(56) References Cited

U.S. PATENT DOCUMENTS

| | | | |
|---|---|---|---|
| 9,585,983 B1 * | 3/2017 | Brahm | ................ A61L 26/009 |
| 9,770,488 B2 * | 9/2017 | Bhatia | .................... A61K 38/39 |
| 2007/0190575 A1 | 8/2007 | Popoff | |
| 2014/0314780 A1 | 10/2014 | Popoff | |
| 2015/0150919 A1 | 6/2015 | Alves Mendes | |
| 2015/0174196 A1 | 6/2015 | Gourdie | |
| 2015/0290289 A1 | 10/2015 | Sampath | |

OTHER PUBLICATIONS

Katayama, A. et al. Beneficial impact of Gpnmb and its significance as a biomarker in nonalcoholic steatohepatitis. Sci. Rep. 5, 16920; doi: 10.1038/srep16920 (2015).*
Yu et al., Journal of Investigative Dermatology, 138:219-227, 2018.*
Yu et al., Abstracts 28th Annual Meeting of the Wound Healing Society, Wound Repairand Regeneration, vol. 24, abstract on p. A30, Apr. 13-17, 2016.*
Yu et al., J Immunol, 192 (1 Supplement) 192.3, May 1, 2014.*
Haemmerle et al., Diabetes 62:2509-2529, 2013.*
Bannon et al., Disease Models & Mechanisms 6, 1434-1447 (2013) doi:10.1242/dmm.012237.*
Yu et al., J. Cell. Biochem. 117(7):1511-1521, Jul. 2016, first published on-line Oct. 7, 2015.*
Kuan et al., Clin Cancer Res, 12(7)1970-1982, 2006.*
International Search Report and Written Opinion dated Aug. 29, 2017 for International Application No. PCT/US17/27402.
Fiorina, Paolo et al. "The mobilization and effect of endogenous bone marrow progenitor cells in diabetic wound healing." Cell transplantation vol. 19,11 (2010): 1369-81. doi:10.3727/096368910X514288.
Gabriel, Tanit L et al. "Lysosomal stress in obese adipose tissue macrophages contributes to MITF-dependent Gpnmb induction." Diabetes vol. 63,10 (2014): 3310-23. doi:10.2337/db13-1720.
Halfon, Svetlana et al. "Markers distinguishing mesenchymal stem cells from fibroblasts are downregulated with passaging." Stem cells and development vol. 20,1 (2011): 53-66. doi:10.1089/scd.2010.0040.
Li, Bing et al. "The melanoma-associated transmembrane glycoprotein Gpnmb controls trafficking of cellular debris for degradation and is essential for tissue repair." FASEB journal: official publication of the Federation of American Societies for Experimental Biology vol. 24,12 (2010): 4767-81. doi:10.1096/fj.10-154757.
Mahdavian Delavary, Babak et al. "Macrophages in skin injury and repair." Immunobiology vol. 216,7 (2011): 753-62. doi:10.1016/j.imbio.2011.01.001.
Tang, Yi et al. "TGF-beta1-induced migration of bone mesenchymal stem cells couples bone resorption with formation." Nature medicine vol. 15,7 (2009): 757-65. doi:10.1038/nm.1979.
Witte, M B, and A Barbul. "General principles of wound healing." The Surgical clinics of North America vol. 77,3 (1997): 509-28. doi:10.1016/s0039-6109(05)70566-1.

* cited by examiner

*Primary Examiner* — Marianne P Allen
(74) *Attorney, Agent, or Firm* — Tarolli, Sundheim, Covell & Tummino LLP

(57) ABSTRACT

A method for treating a skin wound of a subject is described. The method includes contacting the skin wound with a therapeutically effective amount of a wound healing composition comprising glycoprotein nonmelanoma clone B (GPNMB) protein, an active peptide fragment thereof, a GPNMB analog, a GPNMB potentiating agent, or a combination thereof.

15 Claims, 15 Drawing Sheets

GPNMB COMPOSITIONS FOR TREATMENT OF SKIN WOUNDS

RELATED APPLICATION

This application claims the benefit of U.S. Provisional Patent Application Ser. No. 62/321,919, filed Apr. 13, 2016, the entirety of which is hereby incorporated by reference for all purposes.

SEQUENCE LISTING

The instant application contains a Sequence Listing which has been submitted in ASCII format via EFS-Web and is hereby incorporated by reference in its entirety. Said ASCII copy, created on Apr. 22, 2020, is named NEO-Sequence_ST25.txt and is 1,994 bytes in size.

TECHNICAL FIELD

The present application relates generally to compositions and methods for treating and/or promoting wound healing and, more particularly, to potentiating agents, compositions comprising the potentiating agents, and methods employing the compositions that can promote wound repair by, for example, attenuating the production of pro-inflammatory cytokines and enhancing the production of multiple tissue regenerative factors in the wound.

BACKGROUND

Chronic wounds constitute a major health care problem and significantly impair the quality of life for millions of people and impart economic burden on community. There are between 13 to 23 million people suffering from chronic wounds. The annual costs of chronic wound care in the U.S. are estimated to be $25 billion USD. The incidence of chronic wounds is expected to continue on a significant growth trajectory associated with an increase in aging population and prevalence of obesity and diabetes. Several sources estimate that the prevalence of diabetes will rise from 366 million patients in 2011 to 522 million in 2030, and if 5% of all diabetes patients suffer from a chronic wound, then 26 million people would be affected in 2030 by diabetic ulcers alone. This number is significantly high, considering that diabetic ulcers represent only one category of chronic wounds. Furthermore, the prognosis for diabetes ulcer patients remains very poor, whereas wound care for other indications has improved in the past few years.

Current available therapeutics for treating chronic wounds includes debridement to remove necrotic and infected tissues, dressings to provide a moist wound environment, bandages, and topical applications of antimicrobial or biologic agents (growth factors), offloading, physical therapies, and educational strategies. Biological therapies which have been applied to chronic wounds include the applications of growth factors such as platelet derived growth factors (PDGF, such as REGRANEX® gel), keratinocyte growth factor 2 (KGF 2), and gene therapy. A number of other growth factors having the ability to induce wound healing include Vascular Endothelial Growth Factor (VEGF) and basic Fibroblast Growth Factor (bFGF). However, these therapeutic options often fail to achieve complete wound closure. This might be due to that most of these treatments do not readily address the underlying causes of chronic wounds, i.e., persistent inflammation, reduced or non-existent angiogenesis, and tissue remodeling.

SUMMARY

The present application relates generally to compositions and methods for treating and/or promoting wound healing and, more particularly, to potentiating agents, compositions comprising the potentiating agents, and methods employing the compositions that can promote wound repair by, for example, attenuating the production of pro-inflammatory cytokines and enhancing the production of multiple tissue regenerative factors in the wound.

The present invention provides a method for treating a skin wound of a subject, the method comprising contacting the skin wound with a therapeutically effective amount of a wound healing composition comprising glycoprotein non-melanoma clone B (GPNMB) protein, an active peptide fragment thereof, a GPNMB analog, a GPNMB potentiating agent, or a combination thereof. In some embodiments, the wound healing composition comprises GPNMB protein, an active peptide fragment thereof, or a GPNMB analog, while in other embodiments the wound healing composition comprises a GPNMB potentiating agent. In some embodiments, the subject has impaired healing capabilities. For example, a diabetic subject is a subject having impaired healing capabilities.

BRIEF DESCRIPTION OF THE DRAWINGS

The foregoing and other features of the present application will become apparent to those skilled in the art to which the present application relates upon reading the following description with reference to the accompanying drawings, in which:

(FIG. 2A) ELISA analysis for GPNMB expression in wound. The selected day post-wounding is abbreviated as D. n=6. (FIG. 2B) Immunofluorescent images showing co-localization of GPNMB with macrophages. F4/80 (macrophages)=Green, GPNMB=red, and DAPI (nuclei)=blue. Scale bar=10 µm. (FIG. 2C) Quantitative PCR analysis for Gpnmb mRNA in wound macrophages. n=6. (FIG. 2D) A schematic diagram for sorting of CD11b-CD45-CD31-Sca1+CD29+CD146+ cells from wound of mouse using a magnetic-activated cell sorting (MACS). The bright-field microscopic image shows the morphology of sorted CD11b-CD45-CD31-Sca1+CD29+CD146+ cells after 24 hours of culture. (FIG. 2E) Colony forming unit-fibroblast (CFU-F) assay from sorted CD11b-CD45-CD31-Sca1+CD29+CD146+ cells. (FIG. 2F) Photomicrographs of mesenchymal tri-lineage differentiation of wound-isolated CD11b-CD45-CD31-Sca1+CD29+CD146+ cells. (i) Cells were cultured in osteogenic media for 3 weeks, and the mineralized nodules were evaluated by Alizarin Red staining. (ii) Cells were cultured in adipogenic media for 2 weeks, and the accumulation of numerous lipid vesicles within the cells was identified by Oil-red-O staining. (iii) Cells were cultured in chondrogenic media for 3 weeks, and the micromass pellet was stained with toluidine blue. Scale bar=100 μm. (FIG. 2G) Flow cytometric counting of CD11b-CD45-CD31-Sca1+CD29+CD146+ cells from wounded skin. The number of cells is indicated out of 300,000 CD11b-CD45-CD31-wound cells at indicated time points post-wounding. $*p<0.05$;

(FIG. 4A) Expression of Gpnmb mRNA from wounds of D2J/Gpnmb+ and D2J mice. (FIG. 4B) Flow cytometric counting of MSCs from wounds of D2J/Gpnmb+ and D2J mice at 5 days post-wounding. (FIGS. 4C-D) Flow cytometric counting of F4/80+CD86+ (FIG. 4C) and F4/80+CD206+ macrophages (FIG. 4D) from wounds of D2J/Gpnmb+ and D2J mice. (FIGS. 4E-F) The levels of pro-inflammatory cytokines IL-1β (FIG. 4E) (and TNF-α (FIG. 4F) by ELISA at 7 days post-wounding. (FIGS. 4G-H) The levels of pro-healing factors IGF-1 (FIG. 4G) and VEGF (FIG. 4H) by ELISA at 7 days post-wounding. n=6, $*p<0.05$;

(FIG. 6A) Representative photographic images and (FIG. 6B) quantification of the wound closure at selected day post-wounding. (FIG. 6B) Flow cytometric counting of MSCs from wounds of mice (FIGS. 6D-E) Flow cytometric counting of M1 (F4/80+CD86+) (FIG. 6D) and M2 (F4/80+CD206+) macrophages (FIG. 6E) from wounds of mice. (FIGS. 6F-G) The levels of pro-inflammatory cytokines IL-1β (FIG. 6F) and TNF-α (FIG. 6G) in wounds by ELISA. (FIGS. 6H-I) The levels of pro-healing factors IGF-1 (FIG. 6H) and VEGF (FIG. 6I) in wounds by ELISA. n=6, $*p<0.05$;

(FIG. 7B) Flow cytometric counting of MSCs from wounds of D2J/Gpnmb+ mice, D2J mice and D2J mice topically treated with rGPNMB. (FIG. 7C) Expression of pro-inflammatory cytokines iNos, Tnf-α and Il-1b mRNAs in wound-isolated macrophages from C57BL/6 mice with or without rGPNMB treatment. (FIG. 7D) Expression of pro-healing factors Arg-1, Igf-1 and Vegf mRNAs in wound-isolated macrophages from C57BL/6 mice with or without rGPNMB treatment. Data are presented as mean±SEM. n=6, $*p<0.05$;

(FIG. 8A) A schematic diagram for co-culture of bone marrow-derived macrophages and wound-sorted MSCs. M0-polarized macrophages were derived from bone marrow of C57BL/6 mice and wound MSCs were isolated from C57BL/6 mice treated with saline or rGPNMB. The M0 macrophages and wound MSCs were co-cultured for 24 hours and then the expression of CD86 and CD206 were assessed from F4/80+ cells by flow cytometry. (FIGS. 8B-C) The mean fluorescence intensity (MFI) of CD206 (FIG. 8B) and CD86 (FIG. 8C) from F4/80+ macrophages. n=3, $*p<0.05$. (FIG. 8D) A proposed model for cross-talk between wound-infiltrated macrophages and MSCs for immunomodulation and wound repair;

(FIG. 10A) Expression of Gpnmb mRNA in wounds of non-diabetic (db+) and diabetic (db/db) mice post-wounding. (FIGS. 10B-C) Representative photographic images (FIG. 10B) and quantification (FIG. 10C) of wound closure post-wounding from db+ and db/db mice topically treated with Saline or rGPNMB. Wound edge is indicated with red-dotted line. (FIG. 10D) Flow cytometric counting of MSCs from wounds of db/db mice topically treated with Saline or rGPNMB post-wounding. (FIGS. 10E-F) Flow cytometric counting of F4/80+CD86+ (FIG. 10E) and F4/80+CD206+ cells (FIG. 10F) from wounds of db/db mice topically treated with Saline or rGPNMB post-wounding. n=6, $*p<0.05$; (FIG. 11C) A proposed model suggesting that impaired GPNMB activity in diabetic wound environment might contribute to the impaired MSC recruitment and delayed wound healing.

DETAILED DESCRIPTION

Figure 1:
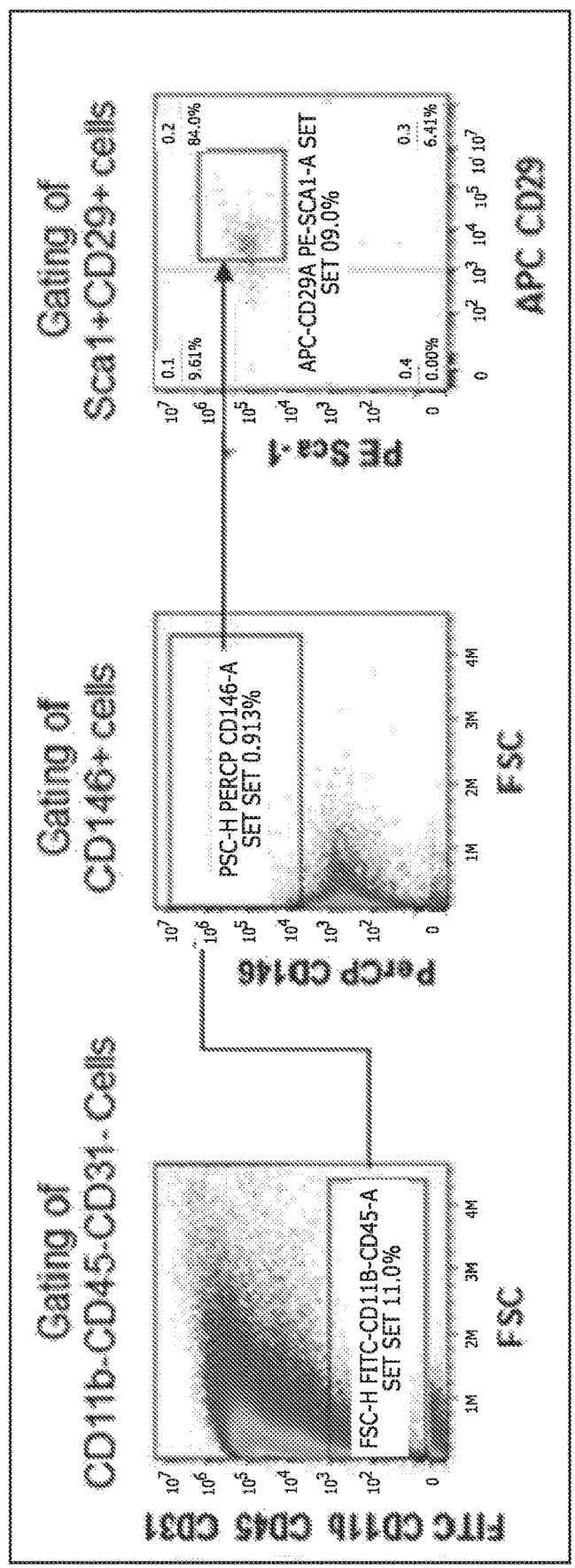
FIG. 1 shows flow cytometry gating strategy for wound MSC counting. Wound cells were gated by excluding CD11b+CD45+CD31+cells. Then, cells were gated by positive selection of CD146+cells. Subsequently, cells were gated by positive selection of both Sca1+ and CD29+ cells. The number of cells were counted out of 300,000 CD11b-CD45-CD31-wound cells.

The present invention provides a method for treating a skin wound of a subject, the method comprising contacting the skin wound with a therapeutically effective amount of a wound healing composition comprising glycoprotein non-melanoma clone B (GPNMB) protein, an active peptide fragment thereof, a GPNMB potentiating agent, or a combination thereof.

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

Also herein, the recitations of numerical ranges by endpoints include all numbers subsumed within that range (e.g., 1 to 5 includes 1, 1.5, 2, 2.75, 3, 3.80, 4, 5, etc.).

A "subject," as used herein, can be any animal, and may also be referred to as the patient. Preferably the subject is a vertebrate animal, and more preferably the subject is a mammal, such as a research animal (e.g., a mouse or rat) or a domesticated farm animal (e.g., cow, horse, pig) or pet (e.g., dog, cat). In some embodiments, the subject is a human.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

"Biocompatible" as used herein, refers to any material that does not cause injury or death to a subject or induce an adverse reaction in a subject when placed in contact with the subject's tissues. Adverse reactions include for example inflammation, infection, fibrotic tissue formation, cell death, or thrombosis. The terms "biocompatible" and "biocompatibility" when used herein are art-recognized and mean that the material is neither itself toxic to a subject, nor degrades (if it degrades) at a rate that produces byproducts (e.g., monomeric or oligomeric subunits or other byproducts) at toxic concentrations, does not cause prolonged inflammation or irritation, or does not induce more than a basal immune reaction in the host.

As used herein, the terms "peptide," "polypeptide" and "protein" are used interchangeably, and refer to a compound comprised of amino acid residues covalently linked by peptide bonds. A protein or peptide must contain at least four amino acids, unless specified otherwise, and no limitation is placed on the maximum number of amino acids that can comprise the sequence of a protein or peptide. Polypeptides include any peptide or protein comprising four or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

All scientific and technical terms used in the present application have meanings commonly used in the art unless otherwise specified. The definitions provided herein are to facilitate understanding of certain terms used frequently herein and are not meant to limit the scope of the present application.

Treatment of Skin Wounds

The present invention provides a method for treating a skin wound of a subject. The method includes contacting the skin wound with a therapeutically effective amount of a wound healing composition comprising glycoprotein non-melanoma clone B (GPNMB) protein, an active peptide fragment thereof, or GPNMB potentiating agent, or a combination thereof. While not intending to be bound by theory, the inventors have shown that GPNMB promotes wound healing as a result of recruitment of mesenchymal stem cells (MSC) to the wound site, and through increased M2 macrophage activity.

As used herein, the term "wound healing" refers to a regenerative process with the induction of an exact temporal and spatial healing program comprising wound closure and the processes involved in wound closure. The term "wound healing" encompasses but is not limited to the processes of granulation, neovascularization, fibroblast, endothelial and epithelial cell migration, extracellular matrix deposition, re-epithelialization, and remodeling.

In some embodiments, the present invention provides methods for "accelerating wound healing," whereby different aspects of the wound healing process are "enhanced." As used herein, the term "enhanced" indicates that the methods provide an increased rate of wound healing. In preferred embodiments, the term "enhanced" indicates that the wound healing rate and/or a wound healing process occurs at least 10% faster than is observed in untreated or control-treated wounds. In particularly preferred embodiments, the term "enhanced" indicates that the wound healing rate and/or a wound healing process occurs at least 15% faster than is observed in untreated or control-treated wounds. In still further preferred embodiments, the term "enhanced" indicates that the wound healing rate and/or a wound healing process occurs at least 20% (e.g., 50%, 100%, . . . ) faster than wounds untreated or control-treated wounds.

Contacting, as used herein, refers to causing two items to become physically adjacent and in contact, or placing them in an environment where such contact will occur within a reasonably short timeframe. For example, contacting a site with a composition comprising GPNMB includes administering the composition (e.g., topical administration) to a subject at or near a site such that the GPNMB will interact with the site to stimulate enhanced bone repair or regeneration. However, contacting also includes systemic administration which results in contact between GPNMB and the skin wound through circulation-mediated contact.

Glycoprotein Non-Melanoma Clone B Protein

In some embodiments, the wound healing composition comprises GPNMB protein, an active peptide fragment thereof, or a GPNMB analog. Glycoprotein non-melanoma clone B (GPNMB) is a type I transmembrane glycoprotein which shows homology to the pMEL17 precursor, a melanocyte-specific protein. GPNMB is encoded by the human GPNMB glycoprotein nmb gene. Two transcription variants, one having 560 amino acids, and the other having 572 amino acids, are known.

GPNMB proteins, peptide fragments thereof, mutants, truncations, derivatives, analogs, and splice variants that display substantially equivalent or altered GPNMB activity relative to the wild-type protein are likewise contemplated for use in the present invention. These variants may be deliberate, for example, such as modifications obtained through site-directed mutagenesis, or may be accidental, such as those obtained through mutations in hosts that are producers of the GPNMB protein. Included within the scope of these terms are GPNMB proteins specifically recited herein, as well as all substantially homologous analogs and allelic variants.

Analogs may be made through substitution of conserved amino acids. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an GPNMB protein is preferably replaced with another amino acid residue from the same side chain family. Alternatively, in another embodiment, mutations can be introduced randomly along all or part of an GPNMB coding sequence, such as by saturation mutagenesis, and the resultant mutants can be screened for GPNMB biological activity to identify mutants that retain activity. Following mutagenesis of the nucleotide sequence for GPNMB, the encoded protein can be expressed recombinantly and the activity of the protein can be determined.

A "non-essential" amino acid residue is a residue that can be altered from the wild-type sequence of GPNMB without abolishing or, more preferably, without substantially altering a biological activity, whereas an "essential" amino acid residue results in such a change. For example, amino acid residues that are conserved among the polypeptides of the present invention are predicted to be particularly unamenable to alteration.

As used herein, an "active peptide fragment" of a GPNMB protein includes a fragment of a GPNMB protein that can accelerate skin wound healing. Biologically active portions of a GPNMB protein include peptides comprising amino acid sequences sufficiently homologous to or derived from the amino acid sequence of a GPNMB protein which include less amino acids than a full length GPNMB proteins and which exhibit at least one activity of an GPNMB protein. A biologically active portion of a GPNMB protein can be a polypeptide which is, e.g., 25, 50, 100, 200 or more amino acids in length.

In some embodiments, the wound healing composition comprises a GPNMB potentiating agent. Potentiation, as used herein, refers to the ability of an agent to increase GPNMB activity. For example, BMP2 and MAP kinase inhibitors are known to increase GPNMB activity. See Rose et al., Clin Cancer Res. 22(24):6088-6098 (2016). Targeting of NFATc2 by small interfering RNA, short hairpin RNA and by an NFATc2 inhibitor also upregulated GPNMB. See Perotti et al., Oncogene, 35(22):2862-72 (2016).

Candidate agents may be tested in animal models. Typically, the animal model is one for the study of wound healing. The study of wound healing in animal models (for instance, mice) is a commonly accepted practice for the study of human wound healing. Results are typically compared between control animals treated with candidate agents and the control littermates that did not receive treatment. Candidate agents can be used in these animal models to determine if a candidate agent increases the rate of wound healing. Candidate agents can also be evaluated for their ability to increase GPNMB activity.

Subjects Having Impaired Healing Capabilities

In some embodiments, the subject receiving treatment has impaired healing capabilities. The term "impaired healing capabilities" refers to subject having wounds which are characterized by a disturbed wound healing process. Examples of subjects having impaired healing capabilities are diabetic patients and alcoholics, obese subjects, patients suffering from deficient blood supply or venous stasis, subjects suffering from estrogen deficiency, and elderly subjects, certain wounds also result in impaired healing capabilities. These include ulcers, wounds which are infected by microorganisms, and ischemic wounds.

In some embodiments, the subject receiving treatment is diabetic. The term "diabetic" as used here refers to subjects having a disorder characterized by the insufficient production or utilization of insulin. Insulin is a pancreatic hormone that is needed to convert glucose for cellular metabolism and energy production. In some embodiments, the term "diabetic patient" refers to patients suffering from diabetes mellitus. The term "diabetic" encompasses both patients with type I diabetes (juvenile onset) and patients with type II diabetes (adult onset). "Type I diabetes" also referred to as "insulin-dependent diabetes" is a form of diabetes mellitus that usually develops during childhood or adolescence and is characterized by a severe deficiency in insulin secretion resulting from atrophy of the islets of Langerhans and causing hyperglycemia and a marked tendency towards ketoacidosis. "Type II diabetes" also referred to as "non-insulin-dependent diabetes" is a form of diabetes mellitus that develops especially in adults (most often in obese individuals) and that is characterized by hyperglycemia resulting from both insulin-resistance and an inability to produce more insulin.

In some embodiments of the invention, the subject receiving treatment exhibits impaired healing capabilities as a result of being elderly. The term "elderly" as used herein refer to older human subjects (e.g., middle age and above of 50 years and older, senior citizen and above of 65 years and older, or elderly and above of 80 years and older, etc.). The term "elderly" also encompass older nonhuman mammalian subjects at similar stages in their life cycles (e.g., 8-12 years and older for cats and large dogs, 10-15 years and older for small and medium sized dogs, 15-18 months and older for mice, etc.).

Wounds

As used herein, the term "wound" refers to a disruption of the normal continuity of structures caused by a physical (e.g., mechanical) force, a biological (e.g., thermic or actinic force, or a chemical means. In particular, the term "wound" encompasses wounds of the skin. The term "wound" also encompasses contused wounds, as well as incised, stab, lacerated, open, penetrating, puncture, abrasions, grazes, burns, frostbites, corrosions, wounds caused by ripping, scratching, pressure, and biting, and other types of wounds. In particular, the term encompasses ulcerations (i.e., ulcers), preferably ulcers of the skin.

In some embodiments, the skin wound being treated is a chronic wound. As used herein, the term "chronic wound" refers to a wound that does not fully heal even after a prolonged period of time (e.g., 2 to 3 months or longer).

In some embodiments, the skin wound being treated is a pressure sore. Pressure sores are also known as bedsores or pressure ulcers. Pressure sores are injuries to skin and underlying tissue resulting from prolonged pressure on the skin. Pressure sores most often develop on skin that covers bony areas of the body, such as the heels, ankles, hips and tailbone.

In some embodiments, the wound being treated is an ulcer. As used herein, the term "ulcer" (i.e., "ulceration") refers to a local defect or excavation of the surface of an organ or tissue, produced by sloughing of necrotic tissue. The term encompasses various forms of ulcers (e.g., diabetic, neuropathic, arterial, decubitus, dental, perforating, phagedenic, rodent, trophic, tropical, varicose, venereal, etc.), although in preferred embodiments, surface (i.e., skin) ulcers are involved in the present invention.

Biocompatible Materials and Wound Care Devices

In some embodiments, the wound healing composition is associated with one or more biocompatible materials, and/or a wound care device. "Wound care devices" include, but are not limited to conventional materials such as dressings, bandages, plasters, compresses, ointments, or gels containing the GPNMB or GPNMB potentiating agent. Wound care devices can be used to facilitate topical and local administration in order to exert an immediate and direct effect on wound healing. "Associated with," as used herein, refers to placement of the wound healing composition in contact (but not bonded to) the biocompatible material or wound care device, or in some cases chemically bonding all or a portion of the wound healing composition to the biocompatible material.

In some embodiments, the wound healing composition is associated with a biocompatible material. As with wound care devices, biocompatible materials can be used to facilitate administration of the GPNMB or GPNMB potentiating agent to a wound. Examples of biocompatible materials include biocompatible polymers; graft materials such as an allograft or xenograft, and natural materials such as collagen.

In some embodiments, the biocompatible material is a polymer. Examples of biocompatible polymers include polymers include natural or synthetic polymers such as polystyrene, polylactic acid, polyketal, butadiene styrene, styreneacrylic-vinyl terpolymer, polymethylmethacrylate, polyethylmethacrylate, polyalkylcyanoacrylate, styrene-maleic anhydride copolymer, polyvinyl acetate, polyvinylpyridine, polydivinylbenzene, polybutyleneterephthalate, acrylonitrile, vinylchloride-acrylates, polycaprolactone, poly (alkyl cyanoacrylates), poly(lactic-co-glycolic acid), and the like.

In some embodiments, the biocompatible material is a biodegradable polylmer. Examples of biodegradable polymers include polylactide polymers include poly(D,L-Lactide)s; poly(lactide-co-glycolide) (PLGA) copolymers; polyglycolide (PGA) and polydioxanone; caprolactone polymers; chitosan; hydroxybutyric acids; polyanhydrides and polyesters; polyphosphazenes; and polyphosphoesters.

Functionalized poly(D,L-Lactide)s can also be used as biodegradable polymers in the nanoparticles of the invention. Examples of functionalized poly(D,L-Lactide)s include poly(L-lactide), acrylate terminated; poly(L-lactide), amine terminated; poly(L-lactide), azide terminated; poly(L-lactide), 2-bromoisobutyryl terminated; poly(L-lactide), 2-bromoisobutyryl terminated; poly(L-lactide) 4-cyano-4-[(dodecylsulfanylthiocarbonyl)sulfanyl]pentonate; poly(L-lactide) N-2-hydroxyethylmaleimide terminated; poly(L-lactide) 2-hydroxyethyl, methacrylate terminated; poly(L-lactide), propargyl terminated; poly(L-lactide), thiol terminated;

Other biodegradable polymers that can be used include AB diblock copolymers such as poly(ethylene glycol) methyl ether-block-poly(D,L lactide); poly(ethylene glycol) methyl ether-block-poly(lactide-co-glycolide) PEG; poly (ethylene glycol)-block-poly(ε-caprolactone) methyl ether PEG; and Polypyrrole-block-poly(caprolactone). Further biodegradable polymers include ABA triblock copolymers such as polylactide-block-poly(ethylene glycol)-block-polylactide PLA; poly(lactide-co-glycolide)-block-poly(ethylene glycol)-block-poly(lactide-co-glycolide); poly(lactide-co-caprolactone)-block-poly(ethylene glycol)-block-poly (lactide-co-caprolactone); polycaprolactone-block-polytetrahydrofuran-block-polycaprolactone; and polyglycolide-block-poly(ethylene glycol)-block-polyglycolide PEG.

Biodegradable polymers also include various natural polymers. Examples of natural polymers include polypeptides including those modified non-peptide components, such as saccharide chains and lipids; nucleotides; sugar-based biopolymers such as polysaccharides; cellulose; chitosan, carbohydrates and starches; dextrans; lignins; polyamino acids; adhesion proteins; lipids and phospholipids (e.g., phosphorylcholine).

In some embodiments, the GPNMB may be disposed on or in the biocompatible material by hand, electro spraying, ionization spraying or impregnating, vibratory dispersion (including sonication), nozzle spraying, compressed-air-assisted spraying, brushing and/or pouring.

In further embodiments, the GPNMB or active peptide fragment thereof is covalently bound to the polymer. The GPNMB or active peptide fragment thereof can be coupled to the polymer either directly or indirectly (e.g. via a linker group). In some embodiments, the GPNMB is covalently attached to a functional group capable of reacting with the GPNMB. For example, a nucleophilic group, such as an amino or sulfhydryl group, can be capable of reacting with a carbonyl-containing group, such as an anhydride or an acid halide, or with an alkyl group containing a good leaving group (e.g., a halide). Alternatively, a suitable chemical linker group can be used. A linker group can serve to increase the chemical reactivity of a substituent on either the GPNMB or the polymer, and thus increase the coupling efficiency.

In some embodiments, the biocompatible material is configured as a tissue scaffold. A tissue scaffold is a support structure that provides a matrix for cells to guide the process of wound healing. The morphology of the scaffold guides cell migration and cells are able to migrate into or over the scaffold, respectively. The cells then are able to proliferate and synthesize new tissue. Examples of biocompatible materials that can be used in a tissue scaffold include allograft, a xenograft, a collagen, and a gelatin. The biocompatible material can be molded or otherwise shaped during preparation to have any desired configuration as a tissue scaffold.

In some embodiments, the scaffold is bioresorbable. Bioresorbable, as used herein, refers to the ability of the scaffolds to be gradually degraded by physiological processes in vivo, to allow the replacement of the biocompatible material with native tissue. For example, if the scaffold is used for wound healing, the scaffold may be gradually degraded while fibroblasts and endothelial cells (for example) form healthy tissue in its place.

The tissue scaffold can be prepared by a variety of methods, depending in part on the nature of the biocompatible material being used. For example, the tissue scaffold may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

Administration of GPNMB

The present invention includes contacting the skin wound with a therapeutically effective amount of a wound healing composition comprising glycoprotein nonmelanoma clone B (GPNMB) protein, an active peptide fragment thereof, a GPNMB analog, a GPNMB potentiating agent, or a combination thereof. The skin wound can be contacted with the active ingredient(s) as a result of placement of a wound care device or suitable biocompatible material including the active ingredient, or it can be administered systemically or locally to the subject.

As used herein, the terms "localized" and "local" refer to the involvement of a limited area. Thus, in contrast to "systemic" treatment, in which the entire body is involved, usually through the vascular and/or lymph systems, localized treatment involves the treatment of a specific, limited area. Thus, in some embodiments, discrete wounds are treated locally using the methods and compositions of the present invention. Topical administration refers to application to the surface of the skin, mucosa, viscera, etc.

In some embodiments, the wound healing composition includes a pharmaceutically acceptable carrier to facilitate administration. The active agent (e.g., GPNMB or GPNMB potentiating agents) is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect (i.e., wound healing), and in a quantity appropriate to achieve the desired daily dose.

Typically, the GPNMB will be suspended in a sterile saline solution for therapeutic uses. The pharmaceutical compositions may alternatively be formulated to provide sustained release of GPNMB locally or systemically. Numerous suitable drug delivery systems are known and include, e.g., implantable drug release systems, hydrogels, hydroxymethylcellulose, microcapsules, liposomes, microemulsions, microspheres, and the like. Sustained release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid. The rate of release of the active ingredient(s) from such a matrix depends upon the molecular weight of the active agent, the amount of the active agent within the matrix, and other factors known to those skilled in the art.

The pharmaceutical composition of this invention may be administered by any suitable means, such as orally, topically, intranasally, subcutaneously, intramuscularly, intravenously, intra-arterially, intraarticulary, intralesionally or parenterally. Ordinarily, topical administration will be preferred. When administered, the wound healing compositions may be combined with other ingredients, such as carriers and/or adjuvants. The GPNMB or other active ingredient(s) may also be covalently attached to a protein carrier, such as albumin, so as to decrease metabolic clearance of the peptides.

It will be apparent to those of ordinary skill in the art that the therapeutically effective amount of GPNMB will depend, inter alia upon the administration schedule, the unit dose of molecule administered, whether the peptide is administered in combination with other therapeutic agents, the immune status and health of the patient, the therapeutic activity of the peptide administered and the judgment of the treating physician.

Although an appropriate dosage of a molecule of the invention varies depending on the administration route, age, body weight, sex, or conditions of the subject, and should be determined by the physician in the end, in the case of oral administration, the daily dosage can generally be between about 0.01 mg to about 500 mg, preferably about 0.01 mg to about 50 mg, more preferably about 0.1 mg to about 10 mg, per kg body weight. In the case of parenteral administration, the daily dosage can generally be between about 0.001 mg to about 100 mg, preferably about 0.001 mg to about 10 mg, more preferably about 0.01 mg to about 1 mg, per kg body weight. The daily dosage can be administered, for example in regimens typical of 1-4 individual administration daily. Dosage administered can also be measured by using a target serum concentration. For example, in some embodiments, a dosage can be administered to provide a serum concentration from 100 ng/mL. to 1000 ng/mL, from 200 ng/mL to 800 ng/mL, from 300 ng/mL to 500 ng/mL, or at least 400 ng/mL. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

The GPNMB can be dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

In some embodiments, a single dose of GPNMB is administered. However, in other embodiments, the GPNMB, GPNMB analog, GPNMB active peptide fragment, or GPNMB potentiating agent is administered repeatedly or continuously over a significant period of time. This can be achieved either through repeated administration, or through use of a sustained-release formulation.

The following example is for the purpose of illustration only and is not intended to limit the scope of the claims, which are appended hereto.

EXAMPLE

Glycoprotein Non-Melanoma Clone B Regulates the Crosstalk Between Macrophages and Mesenchymal Stem Cells Towards Wound Repair The process of wound repair requires the coordinated participation of multiple types of cells, which are sequentially recruited during the healing process. In response to tissue injury, both macrophages and mesenchymal stem cells (MSCs) are recruited to the site of injury, where they participate in the repair process. Despite considerable understanding on the role of each cell type in the process of wound repair, the nature of dynamic interplay between these two cell types and how this interaction influences the functional activities for MSCs towards wound repair are not well understood. Here, using a mouse model of skin wound healing, we provide evidence that macrophages-derived glycoprotein non-melanoma clone B (GPNMB) is functionally important in promoting the recruitment of MSCs to the site of skin injury, which in turn modulate inflammatory response by directing the M2 polarization of macrophages in acute wound healing. We further demonstrate that GPNMB signaling is impaired in diabetic wound environment, which is associated with impaired MSC recruitment and delayed wound healing. Importantly, topical administration of recombinant GPNMB protein could reverse the impaired MSC response and wound closure in diabetic mice.

Materials and Methods

Animals

Wild-type C57BL/6, diabetic db/db (BKS.Cg-Dock7$^{m\ +/+}$ Lepr$^{db}$/J) and non-diabetic db/+ (heterozygotes Lepr$^{db}$/+) mice were obtained from Jackson Laboratories. Gpnmb-control D2J/Gpnmb+ and Gpnmb-mutant DBA/2J (D2J) mice were obtained from Charles River and Jackson Laboratories, respectively. Male mice at ages of 8-10 weeks old were used for all the experiments. The experimental protocol was reviewed and approved by the Institutional Animal Care and Use Committee of Kent State University.

Excisional Skin Wounding, Topical Treatment of rGPNMB, and Wound Size Measurement Mice were anesthetized with 1.5% isoflurane gas inhalation and one full-thickness, circular wound was made on the dorsal surface of each mouse using a 8 mm sterile biopsy punch (Acuderm Inc). The wound was gently applied with sterile wound dressing (collagen sponge, Medline) soaked with sterile saline for Saline control group or rGPNMB (R&D, 2 µg per wound) for rGPNMB treatment group. Then, the wound area was covered with a transparent, semipermeable dressing (Tegaderm, 3M) to allow for daily inspection of the wound and protection from infection. Photographs of wounds were taken at the same distance by a digital camera and the extent of wound closure at a given time point was normalized as a percent change with respect to the initial wound size at day 0. The wound size was measured using an image analysis software (Motic 3.0). At the indicated time point, mice were euthanized by $CO_2$ inhalation for the collection of wounded skin tissue. For selected group of mice, bone marrow cells were collected as described (Yu et al., 2016).

Immunofluorescence Microscopy

Frozen sections of skin wounds were fixed in freshly prepared cold acetone for 20 minutes on ice and then treated with 0.3% Triton X-100/PBS at room temperature for 20 minutes. Sections were incubated with 5% goat serum (Sigma-Aldrich) for 30 minutes and then incubated with primary antibodies at 4° C. overnight. The next morning, slides were washed with PBS and incubated with secondary antibodies for 45 minutes at room temperature. Sections were then washed and mounted with VectaShield Mounting Medium with DAPI. Microscopic images were taken with an Olympus X81 microscope. Primary and secondary antibodies used were as follows: F4/80 (1:100, Abcam), GPNMB (1:500, R&D), Alexa Fluor 594 goat anti-mouse IgG1 (1:500, Invitrogen), and Alexa Fluor 488 goat anti-rabbit IgG (1:500, Invitrogen).

Magnetic-Activated Cell Sorting (MACS) of Cells From Wounds of Mice

Cells were dissociated from excisional wounds of mice using an enzymatic digest with collagenase I, collagenase XI and hyaluronidase (Sigma-Aldrich). For the isolation of macrophages, wound cells were incubated with Biotin-F4/80 antibody (BioLegend) and washed with washing buffer. Then, cells were incubated with anti-Biotin microbead (Miltenyi Biotec) and F4/80 positive cells were positively selected by MACS magnetic column (Miltenyi Biotec). The sorted cells were validated by flow cytometry, in which greater than 96% of cells were F4/80 positive. For the isolation of MSCs from wound cells, sequential MACS were performed with MultiSort Kits (Miltenyi Biotec). Firstly, cells dissociated from mouse wound were incubated with PE-CD31, PE-CD11b and PE-CD45 antibodies (BioLegend) and washed with washing buffer. Then, cells were subsequently incubated with anti-PE microbead (Miltenyi Biotec) and CD31-CD11b-CD45-cells were negatively selected by MACS magnetic column by depleting cells positive for CD31, CD11b, or CD45. Subsequently, Sca-1 positive cells were positively selected from the sorted CD31-CD11b-CD45-cells by FITC-Sca-1 antibody/Anti-FITC MultiSort Kit (Miltenyi Biotec). Then, the sorted cells were treated with APC-CD29 antibody (BioLegend)/Anti-APC MultiSort Kit (Miltenyi Biotec) to positively select CD29 cells. Lastly, the sorted CD31-CD11b-CD45-CD29+ Sca-1+ cells were incubated with Biotin-CD146 antibody (Miltenyi Biotec) and cells were positively selected by anti-Biotin microbeads and magnetic column (Miltenyi Biotec) to yield CD31-CD11b-CD45-Sca1+CD29+CD146 cells.

Flow Cytometry

Antibodies were obtained from BioLegend. For the identification of M1- or M2-polarized macrophages from wound, cells dissociated from mouse wound were stained with APC-labeled anti-F4/80 antibody to identify macrophages and further stained with PE-labeled anti-CD206 antibody to identify M2 polarization or PerCP-labeled anti-CD86 antibody to identify M1 polarized macrophages. Then, stained cells were analyzed by flow cytometry (Accuri C6, BD Biosciences). For the identification of MSCs (CD11b-CD45-CD31-CD146+Sca1+CD29+ cells) from wounded skin, cells dissociated from mouse wound were incubated with FITC-CD11b, FITC-CD45, FITC-CD31, PE-Sca-1, APC-CD29, and PerCP-CD146 antibodies. Firstly, wound MSCs were negatively gated by FITC positive cells to exclude cells positive for CD11b, CD45, and CD31. Subsequently, cells positive for CD146 were gated and then cells positive for both Sca-1 and CD29 were selected (FIG. 1). In the analysis, the threshold for fluorescence positive cells for each antigen were set by comparison to the measurements for IgG controls.

Colony Forming Unit-Fibroblast (CFU-F) Assay

About 100 of MACS-sorted CD11b-CD45-CD31-CD146+Sca1+CD29+ cells from wounds of mouse were plated into 100 mm plate with 10 ml of α-MEM supplemented with glutamine (2 mM), penicillin (100 U/ml), streptomycin sulfate (100 mg/ml), and 20% lot-selected FBS. Triplicate cultures were established. On day 7, cultures were fixed and stained with 0.5% crystal violet. The colonies containing 50 or more cells were counted.

Tri-Lineage Differentiation Assays

For osteogenic differentiation, MACS-sorted CD11b-CD45-CD31-CD146+Sca1+CD29+ cells from skin wounds were seeded at a density of $5 \times 10^3/cm^2$ with α-MEM supplemented with 10% FBS, $10^{-7}$M dexamethasone (Sigma-Aldrich), 10 mM β-glycerol phosphate (Sigma-Aldrich), and 50 mM ascorbate-2-phosphate (Sigma-Aldrich). Cultures in α-MEM supplemented with 10% FBS served as a negative control. After 3 weeks of differentiation, the mineralization capacity of the cells was evaluated by Alizarin Red staining (2% of Alizarin Red S (Sigma-Aldrich) dissolved in water with the pH adjusted to 4.2). For adipogenic differentiation, cells were seeded at a density of $1-3 \times 10^4/cm^2$ with α-MEM supplemented with 10% FBS, $10^{-6}$M dexamethasone, 0.5 mM IBMX (Sigma-Aldrich), and 10 ng/ml of insulin (Sigma-Aldrich) for 2 weeks. Cultures of cells in α-MEM supplemented with 10% FBS served as a negative control. Lipid accumulation was identified by Oil-red-O staining (0.5 g of Oil-red-O (Sigma-Aldrich). For chondrogenic differentiation, cells ($2 \times 10^5$) were seeded in polypropylene tubes with high-glucose D-MEM supplemented with $10^7$ M dexamethasone, 1% ITS, 50 mM ascorbate-2-phosphate, 1 mM sodium pyruvate, 50 mg/ml of proline (all from Sigma-Aldrich), and 20 ng/ml of TGF-β3 (R&D Systems). Culture of cells in high-glucose D-MEM supplemented with 10% FBS served as a negative control. After 3 weeks in culture, the pellets were fixed in 10% buffered formalin for 48 hours and embedded in paraffin. Then 4 mm thick sections were processed for toluidine blue staining (1 g of toluidine blue Sigma-Aldrich) was dissolved in 100 ml of 70% alcohol and diluted to 10% with 1% sodium chloride, pH adjusted to 2.3).

Co-Culture of Macrophage and MSCs

MSCs were MACS-sorted from wounds of C57BL/6 mice as described above. Monocytes were isolated from bone marrow of C57BL/6 mice and differentiated into M0-polarized macrophages by stimulating the cells with recombinant murine macrophage-colony stimulating factor (M-CSF, 20 ng/ml, Peprotech) for 6 days. The M0 macrophages were seeded onto 12-well plate. Then, $1\times10^4$ MSCs were co-cultured with $1\times10^5$ M0 macrophages for 24 hours and cells of co-culture were detached and incubated with Biotin conjugated anti-mouse F4/80 antibody (eBioscience) on ice for 30 minutes. Cells were washed by MACS buffer and then incubated with anti-Biotin microbeads (Miltenyi Biotec) and F4/80 positive cells were positively selected by MACS magnetic column as described above. Isolated macrophages were stained by PE conjugated anti-CD206 and APC conjugated anti-CD86 antibodies (BioLegend) and mean fluorescence intensity were quantified by flow cytometry.

qPCR Analysis

Total RNA was isolated from wound cells or wound-sorted macrophages using the MicroElute Total RNA Kit (Omega). RNA (500 ng) was reverse-transcribed using the qScript™ cDNA SuperMix (Quanta), and subjected to qPCR with PerfeCTa SYBR Green SuperMix. Gene expression was normalized to GAPDH using the $\Delta\Delta Ct$ method. The primers for Gpnmb, M1 marker (iNos), M2 markers (Arg-1, cd206), pro-inflammation cytokines (Tnf-$\alpha$, Il-1$\beta$), and pro-healing factors (Igf-1, Vegf) were synthesized by Integrated DNA Technologies.

ELISA

Wound tissues collected at indicated time points were homogenized in 350 µl of cold tissue extraction buffer supplemented with protease inhibitor cocktail (Sigma-Aldrich) using a rotor-stator homogenizer. The extracts were agitated at 4° C. for 2 hours then centrifuged at 10,000 g and supernatants were used for ELISA assay. The protein levels of GPNMB (R&D), IL-1$\beta$, TNF-$\alpha$, IGF-1, and VEGF (BioLegend) were measured in sample supernatants using ELISA kits.

Statistics

All results are expressed as the mean±SEM. The Student's unpaired t test was used for comparisons between two groups. One-way analysis of variance (ANOVA) followed by Bonferroni's post-hoc test was used for comparisons between multiple groups. $P<0.05$ was considered to be statistically significant.

Results

Figure 2A:
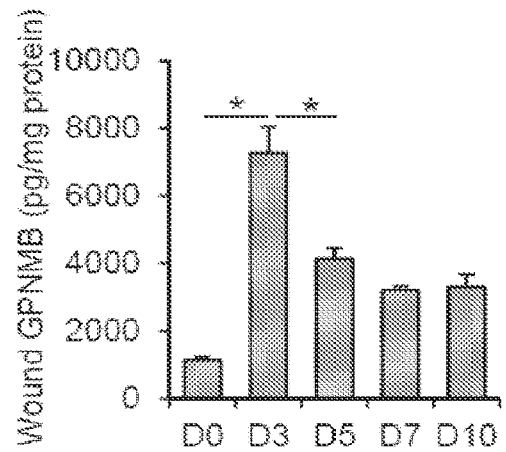
FIGS. 2A-G show expression of GPNMB and recruitment of MSCs following skin wounding from C57BL/6 mice.
Figure 2B:
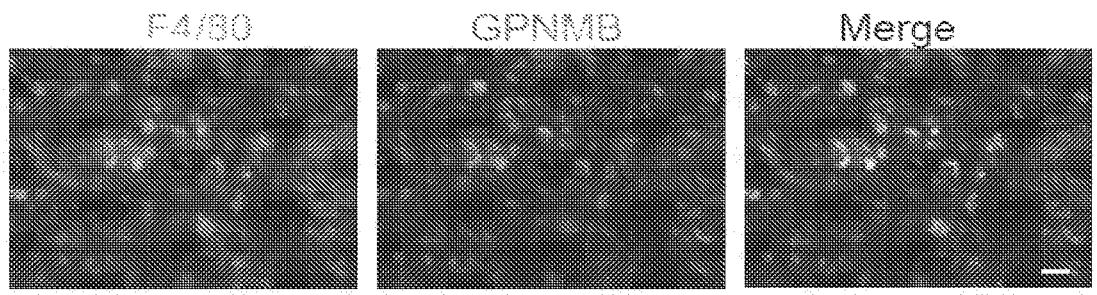
Figure 2C:
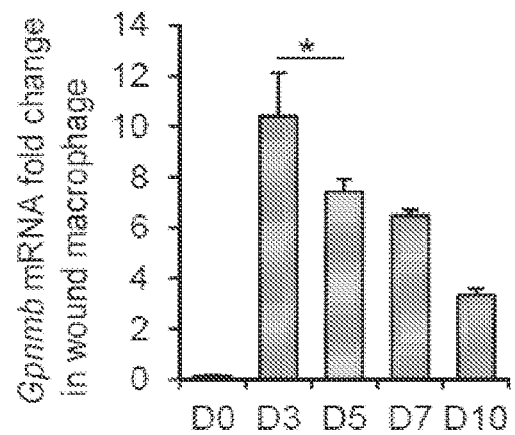
Figure 3:
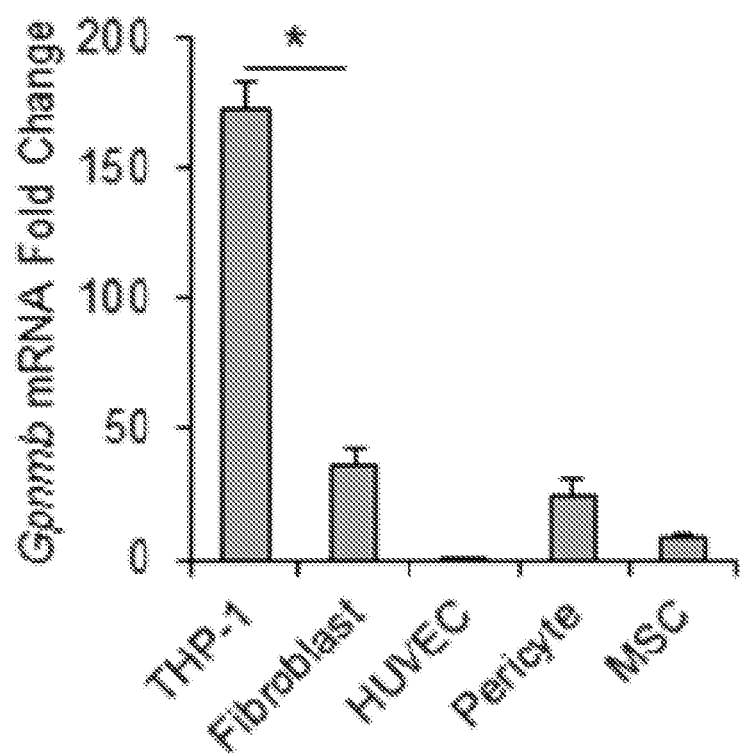
FIG. 3 shows expression of Gpnmb mRNA from human cell lines. Total RNAs were collected from THP-1 monocytes (ATCC), human dermal fibroblast (Lonza), HUVEC (Lonza), human pericyte (Promo Cell) and bone marrow-derived human MSCs (Promo Cell) and the expression of Gpnmb mRNAs were compared. n=3. Data are presented as mean±SEM. $*p<0.05$.

Skin Wounding Elicits the Increased Expression of GPNMB From Macrophages in Wounds of Wild-Type Mice To determine the role of GPNMB in wound healing, we first examined the expression of GPNMB from wounds of C57BL/6 mice. The levels of GPNMB protein in unwounded skin tissue were only weakly detected (FIG. 2A). After skin wounding, the secretion of GPNMB protein was significantly increased by reaching the maximal level at day 3 post-wounding and then gradually decreased over the course of wound repair (FIG. 2A). We next engaged in a study to identify the source of cells that express GPNMB following skin wounding using immunofluorescence analysis of wounded skin. Immunofluorescence images show that GPNMB positive cells were preferentially co-localized with F4/80 positive macrophages, whereas other type of cells stained with DAPI were negative for GPNMB staining (FIG. 2B). To confirm whether macrophage is the major source of cells for GPNMB expression in the wound bed, the expression of Gpnmb mRNA was quantified from macrophages isolated from skin wounds (FIG. 2C). The kinetics of Gpnmb mRNA in wound macrophages exhibits a close correlation with protein levels of GPNMB in the wound. To further confirm this and whether this phenomena is also true for human cells, we compared the relative expression of Gpnmb mRNA from several types of human cells involved in skin wound healing. The expression of Gpnmb mRNA was significantly higher in THP-1 monocytes than other type of cells including fibroblasts, bone marrow-derived human MSCs, human umbilical vein endothelial cells (HUVECs) and human pericytes (FIG. 3). This is consistent with reported studies that demonstrate macrophage as a major source of cells for secreting GPNMB (Gabriel et al., 2014; Katayama et al., 2015; Li et al., 2010).

Figure 2D:
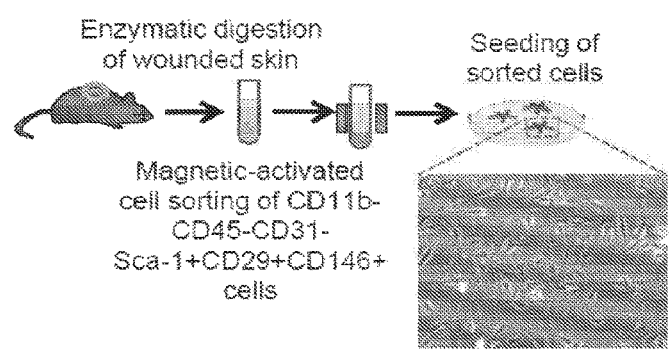
Figure 2E:
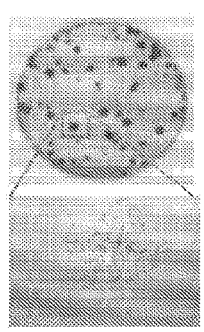
Figure 2F:
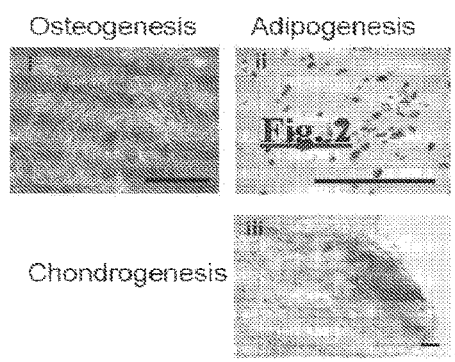
Figure 2G:
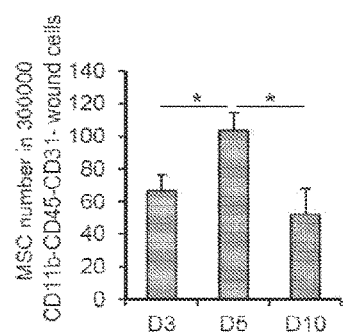

Wound-Infiltrated CD11b-CD45-CD31-Sca-1+CD29+CD146+ Cells Exhibit MSC Characteristics of Self-Renewal and Differentiation To identify endogenous MSCs that are infiltrated to the wound, we have used three negative markers of CD11b, CD45, and CD31 and three positive markers of Sca-1, CD29, and CD146 (Tang et al., 2009). MSCs are negative for hematopoietic lineage markers of CD45 and CD11b, whereas both Sca-1 and CD29 have been considered to be typical MSC markers. In addition, in this study, we have used CD31 as a negative marker to exclude endothelial cells and CD146 as a positive marker to differentiate MSC from fibroblast (Halfon et al., 2011). Then, we examined whether CD11b-CD45-CD31-Sca-1+CD29+CD146+ cells can indeed exhibit characteristics of MSCs. For this, CD11b-CD45-CD31-Sca-1+CD29+CD146+ cells were isolated from wounds of C57BL/6 mice at day 5 post-wounding by magnetic activated cell sorting (MACS). The sorted cells were plated and cultured on tissue-culture dish. At day 1, the sorted cells exhibited a spindle-shape morphology of MSCs (FIG. 2D). The colony forming unit-fibroblast (CFU-F) assay demonstrated a proliferative capacity of the wound-sorted CD11b-CD45-CD31-Sca-1+CD29+CD146+ cells (FIG. 2E). The MSC characteristic of the sorted cells were further confirmed by their tri-mesenchymal lineage differentiation capacity towards osteogenesis, adipogenesis, and chondrogenesis (FIG. 2F). These results support that wound infiltrated CD11b-CD45-CD31-Sca-1+CD29+CD146+ cells are indeed MSCs that satisfy characteristic of self-renewal and tri-mesenchymal lineage differentiation. After identifying MSCs in the wound, we next quantified the kinetics of MSCs recruitment over the course of wound healing using a flow cytometric identification and counting of CD11b-CD45-CD31-Sca-1+CD29+CD146+ cells (FIG. 1). Our data shows that skin wounding resulted in transient increase in MSC number in the wound, which peaked at day 5 post-wounding (FIG. 2G). Since macrophages appear in the wound within day 2 and reach a peak as early as day 3 post-wounding (Mandavian Delavary et al., 2011; Witte and Barbul, 1997), our data implicates that the trafficking of macrophages may precede the appearance of MSCs in the wound. Taken together, our results show that skin wounding elicits the increased expression of GPNMB from macrophages in the wound, which is associated with the recruitment of MSCs.

Figure 4:
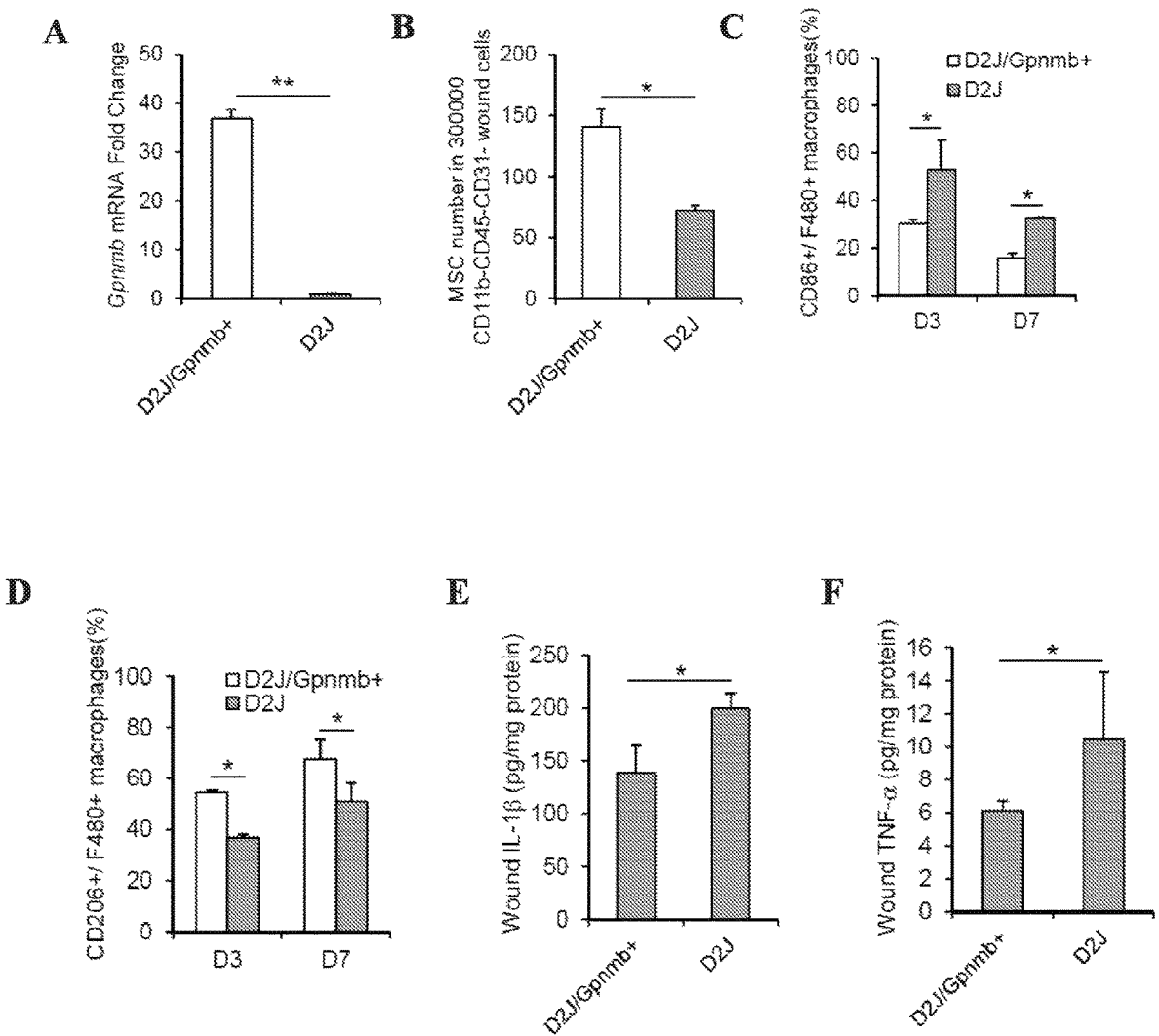
FIGS. 4A-H show the effect of GPNMB deficiency on the recruitment of MSCs, wound closure, and macrophage polarization in response to skin wounding. Excisional wounds in control D2J/Gpnmb+ mice and Gpnmb− mutant (D2J) mice were harvested at selected day post-wounding.
Figure 4:
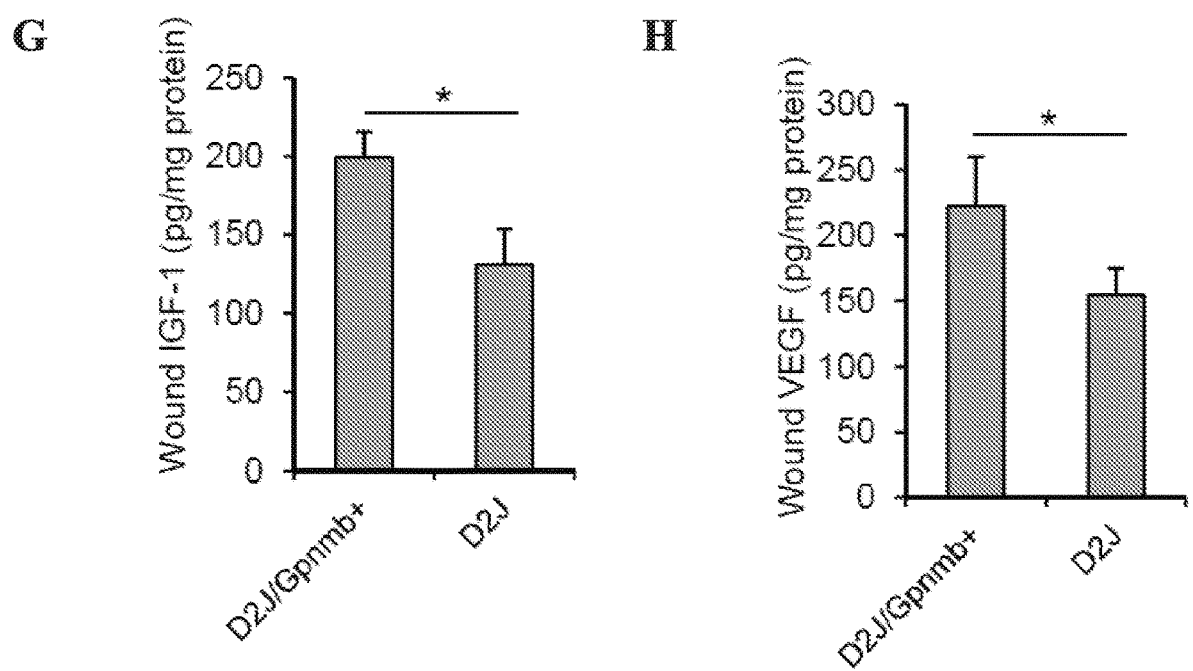
Figure 5:
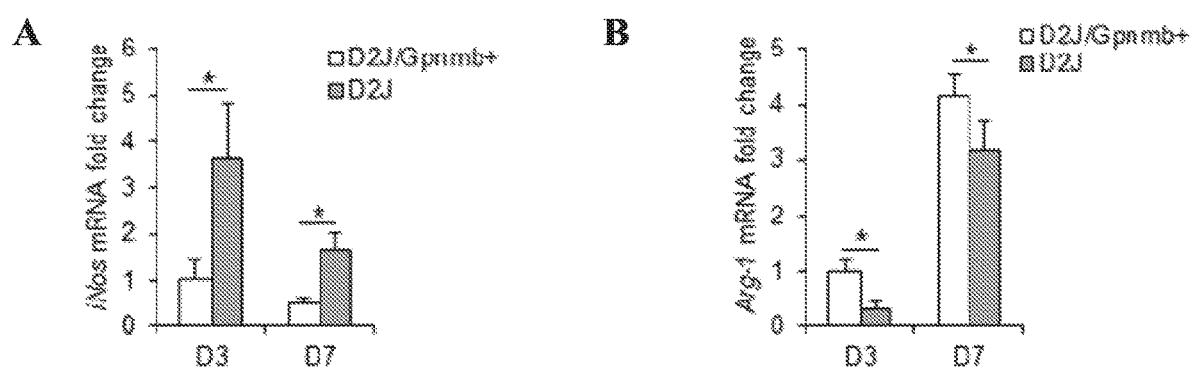
FIGS. 5A-B show the expression of M1 marker iNos (FIG. 5A) and M2 marker Arg-1 (FIG. 5B) from wound-isolated macrophages at 7 day after wounding were compared between D2J/Gpnmb+ and D2J mice. Data are presented as mean±SEM. n=6, $*p<0.05$.

The Deficiency of GPNMB Impairs the Recruitment of MSCs and Prolongs Inflammation Following Skin Wounding With our observations of the increased expression of GPNMB and number of MSCs in the wound following skin wounding, we next explored whether the increased expression of GPNMB to skin wounding is functionally important in the recruitment of MSCs to the wound. This was performed by quantifying the extent of MSC recruitment and wound closure from Gpnmb-mutant (D2J) and Gpnmb-control (D2J/Gpnmb+) mice. The expression of Gpnmb mRNA was negligible in wounds of Gpnmb-mutant mice (FIG. 4A). Gpnmb-mutant mice exhibited an attenuated number of MSCs in the wound by ~40%, compared to littermate controls at day 5 post-wounding (FIG. 4B). The flow cytometric analysis of cells from skin wounds revealed that wounds of Gpnmb-mutant mice exhibited increased trafficking of M1 macrophages (F4/80+CD86+ cells) and attenuated trafficking of M2 macrophages (F4/80+CD206+ cells) in the wound, compared to control mice (FIGS. 4C-D). This was further confirmed by decrease in the expression of M1 marker, inducible nitric oxide synthase (iNOS), and increase of M2 marker, arginase 1 (Arg-1) (FIGS. 5A-B). In addition, wounds of Gpnmb-mutant mice were associated with prolonged accumulation of the pro-inflammatory cytokines including interleukin-1β (IL-1β) and tumor necrosis factor-α (TNF-α) (FIGS. 4E-F) and reduced levels of pro-healing factors including insulin-like growth factor-1 (IGF-1) and vascular endothelial growth factor (VEGF) (FIGS. 4G-H). Taken together, these results indicate that loss of GPNMB activity in wounds diminishes the recruitment of MSCs and prolongs inflammation associated with increased trafficking of M1 macrophages.

Figure 6:
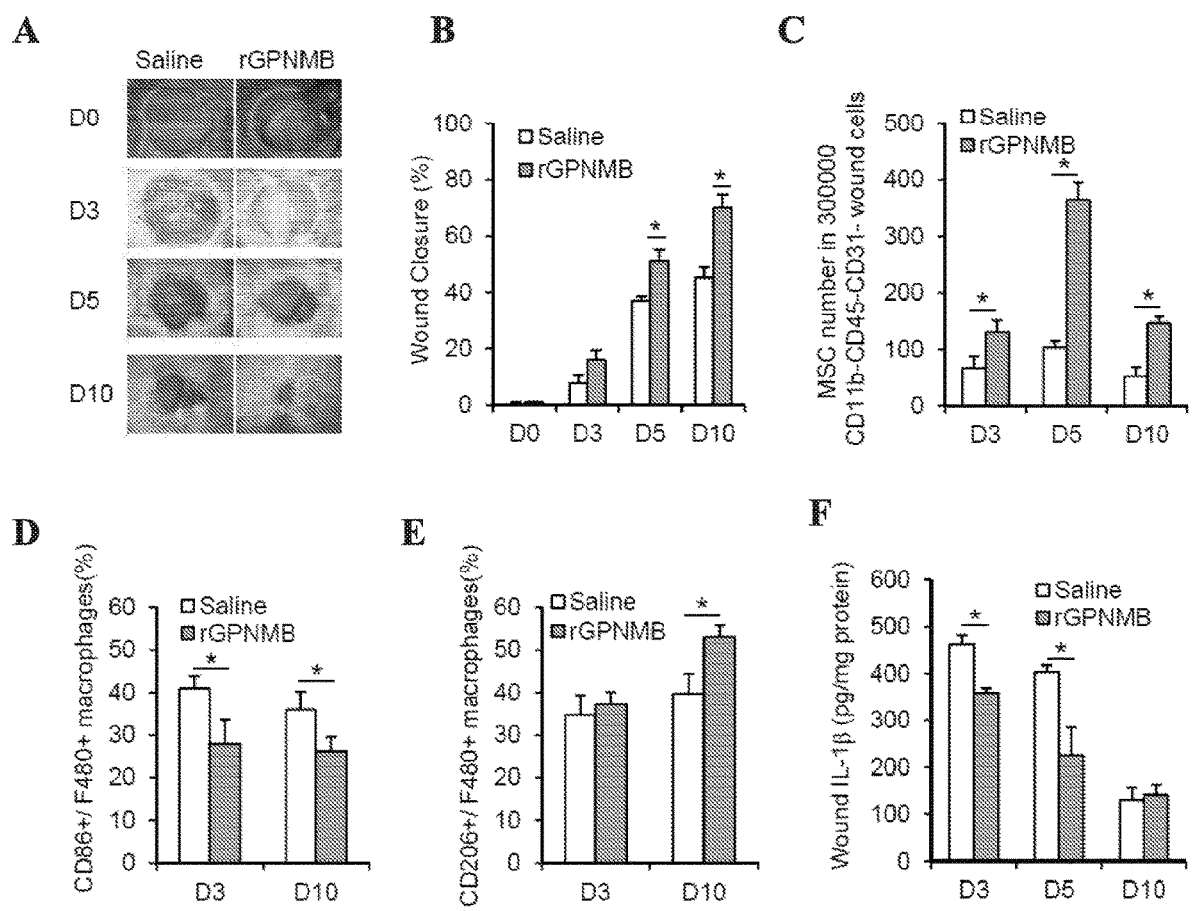
FIGS. 6A-I show the effect of topical treatment of rGPNMB on the MSC recruitment and wound closure in C57BL/6 mice. Wounds of C57BL/6 mice were topically treated with saline or rGPNMB (2 μg per wound) immediately after skin wounding at day 0.
Figure 6:
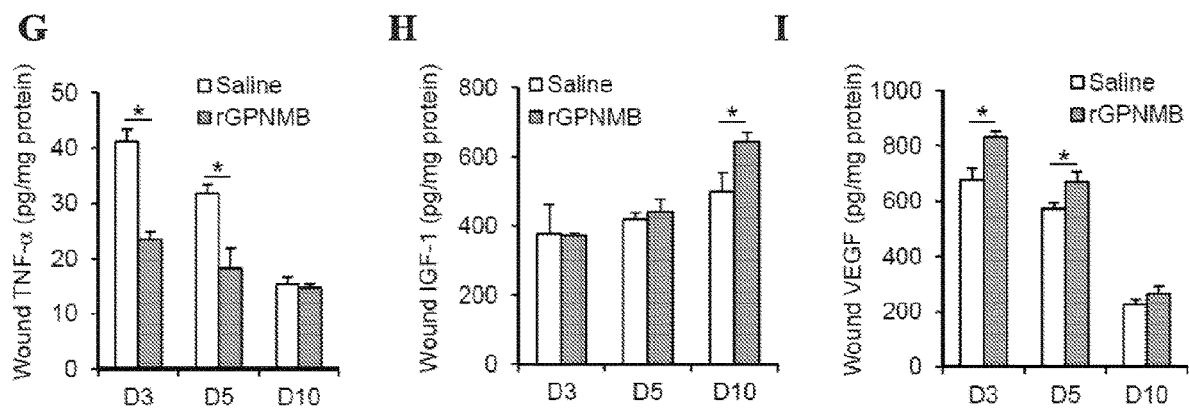
Figure 7:
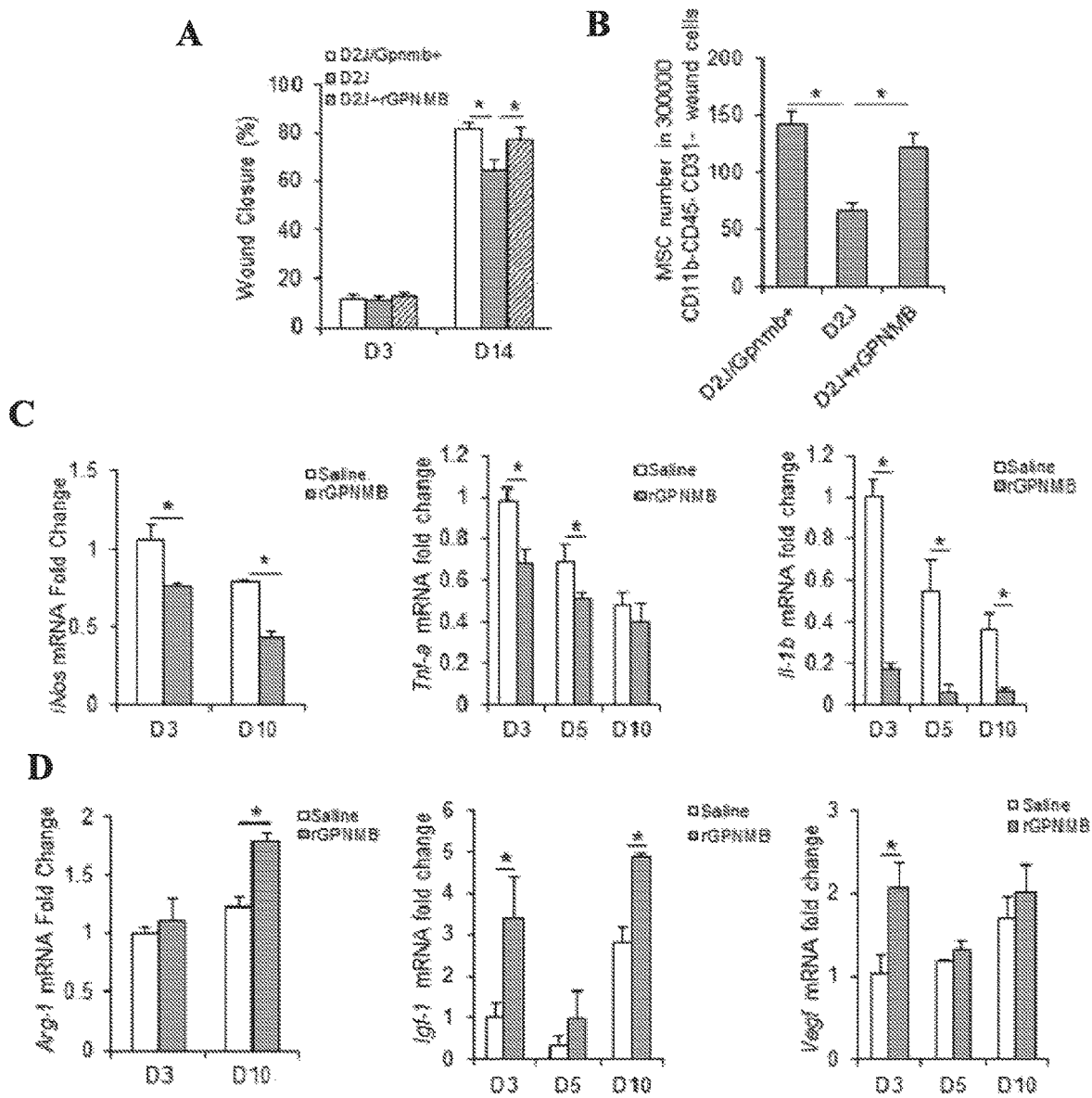
FIGS. 7A-D show (FIG. 7A) Quantification of the wound closure at days 3 and 14 after wounding in D2J/Gpnmb+ mice, D2J mice and D2J mice topically treated with rGPNMB (2 μg per wound).

The Increased Expression of GPNMB Following Skin Wounding is Functionally Important in Recruiting MSCs to the Wound We next examined whether increasing the availability of GPNMB in the wound restores the recruitment of MSCs to the wound. This was assessed by topically applying rGPNMB to the wound, which mimics the soluble form of extracellular fragment of GPNMB protein. We previously demonstrated the capacity of rGPNMB in promoting the migration of MSCs from in vitro study (Yu et al., 2016). The topical treatment of rGPNMB to the wounds of C57BL/6 wild-type mice could significantly accelerate wound closure (FIGS. 6A-B) and increase the number of MSCs in the wound by 3-fold at day 5 post-wounding (FIG. 6C). In consistent with the finding from C57BL/6 mice, the topical treatment of rGPNMB to the wounds of Gpnmb-mutant mice restored the extent of wound closure (FIG. 7A) and MSCs recruitment (FIG. 7B). The improved MSCs response to rGPNMB treatment in C57BL/6 mice was associated with decrease in F4/80+CD86+(M1) macrophages and increase in F4/80+CD206 (M2) macrophages in the wound (FIGS. 6D-E). This was further confirmed by gene expression analysis showing the decreased expression of M1 markers (iNOS, IL-1β, Tnf-a, FIG. 7C) and increased expression of M2 markers (Arg-1, Igf-1, Vegf, FIG. 7D) in macrophages isolated from wounds of mice treated with rGPNMB, compared with control mice. The increased recruitment of MSCs and M2 macrophages were associated with reduction in pro-inflammatory cytokines including IL-Iβ and TNF-α (FIGS. 6F-G) and increased levels of pro-healing factors including IGF-1 and VEGF (FIGS. 6H-I). Taken together, these results strongly support that the increased expression of GPNMB to skin wounding is functionally important in promoting the recruitment of endogenous MSCs and trafficking of M2 macrophages to the wound, which might trigger pro-healing responses subsequently.

Wound-Infiltrated MSCs are Capable of Promoting M2 Polarization of Macrophages

Figure 8:
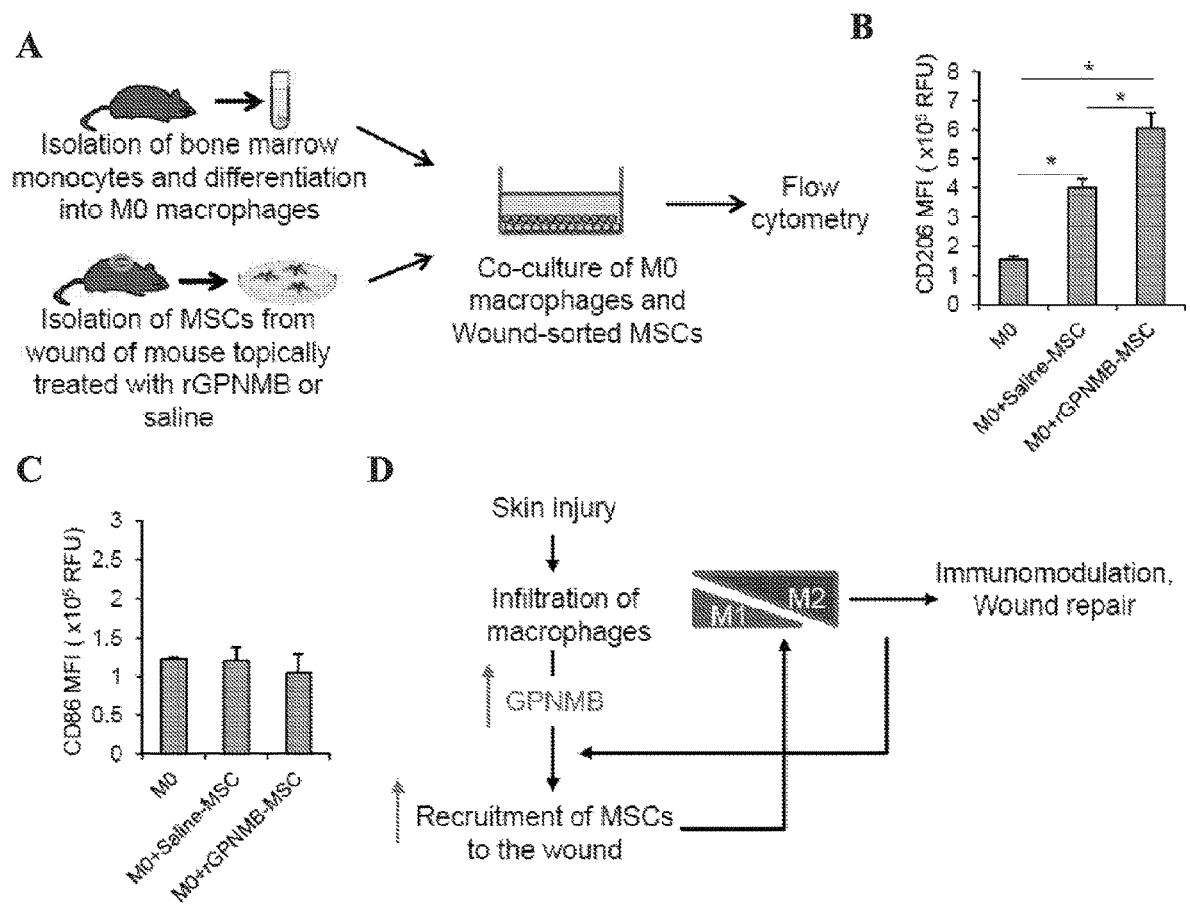
FIGS. 8A-D show the effect of wound-infiltrated MSCs on the polarization of macrophages.
Figure 9:
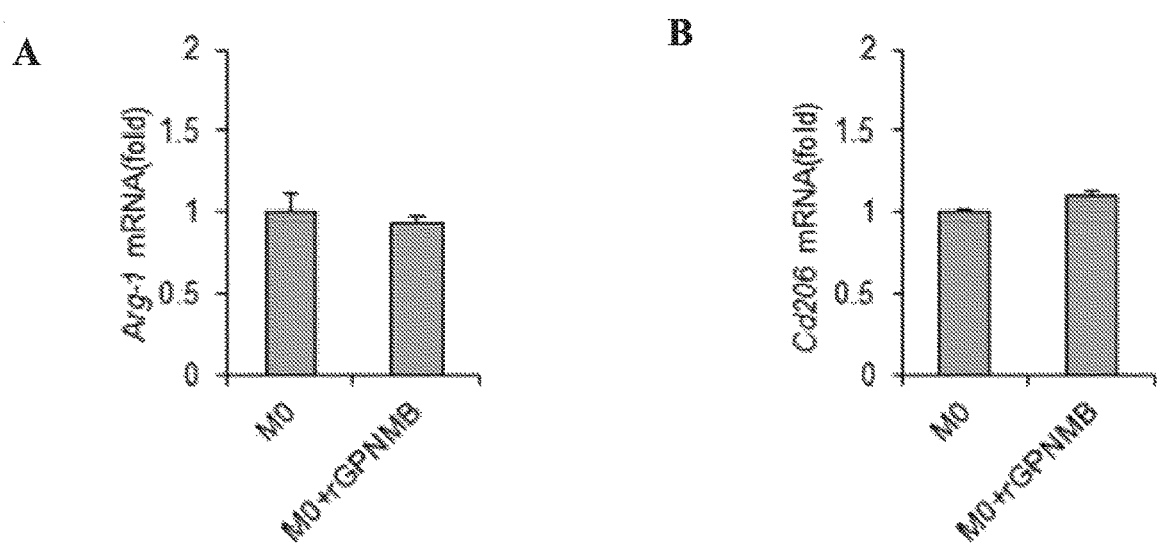
FIGS. 9A-B show the effect of rGPNMB treatment on M2 polarization of macrophages. M0-polarized macrophages were treated with 50 ng/ml rGPNMB for 24 hours then the expression of M2 marker genes Arg-1 (FIG. 9A) and Cd206 (FIG. 9B) were assessed by qPCR. n=3. Data are presented as mean±SEM.

By observing the increased trafficking of M2 macrophages, along with increased recruitment of MSCs to the wounds, with the topical treatment of rGPNMB, we next examined whether wound-infiltrated MSCs are responsible for enhanced M2 response. For this, MSCs were isolated from wounds of C57BL/6 mice, sorted with MACS and co-cultured with M0-polarized macrophages isolated from bone marrow of C57BL/6 mice (FIG. 8A). The ex-vivo co-culture of M0 macrophages and MSCs revealed that wound infiltrated MSCs have the capacity to promote M2 polarization of macrophages as assessed by the increased expression of M2 marker (CD206) from macrophages. Importantly, the extent of M2 polarization was further enhanced for co-culture with MSCs isolated from wounds of mice treated with rGPNMB (FIG. 8B). However, there was no significant difference in the expression of M1 marker CD86 in the presence of MSCs (FIG. 8C). The direct treatment of rGPNMB to the macrophages alone did not increase the expression of M2 markers, as assessed by the expression of Arg-1 (FIG. 9A) and Cd 206 mRNAs (FIG. 9B), suggesting that the action of rGPNMB to promote M2 polarization is mediated by MSCs, not by autocrine action of macrophages. Along with our observation that macrophages are major source of GPNMB secretion in the wound (FIG. 2C), these results suggest that GPNMB released from wound-infiltrated macrophages following skin wounding promotes the recruitment of MSCs to the wound, which may in turn act on macrophages to direct the polarization of macrophages toward the M2 phenotype (FIG. 8D).

Figure 10:
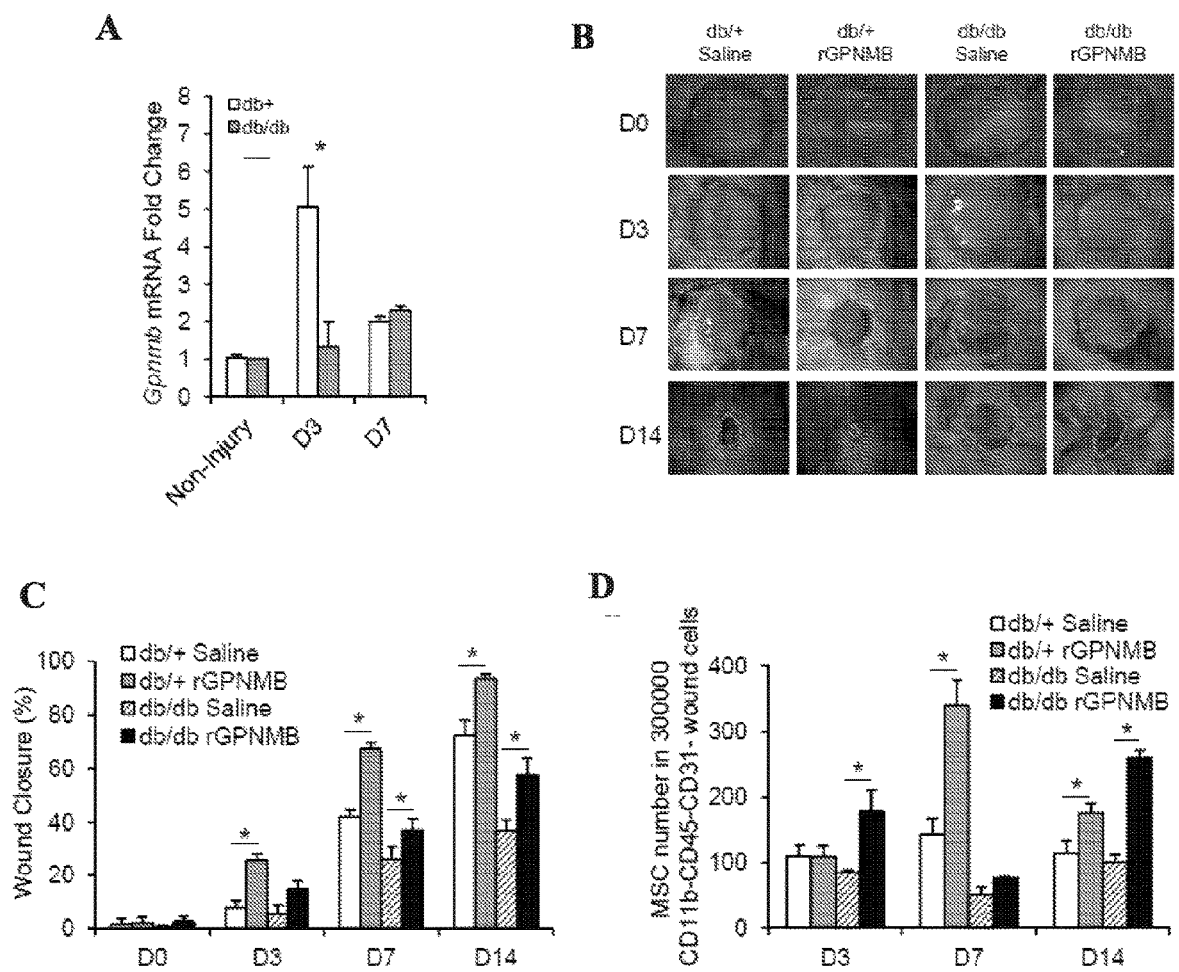
FIGS. 10A-F show the role of GPNMB in the recruitment of MSCs, wound closure, and macrophage polarization in wounds of diabetic mice.
Figure 10:
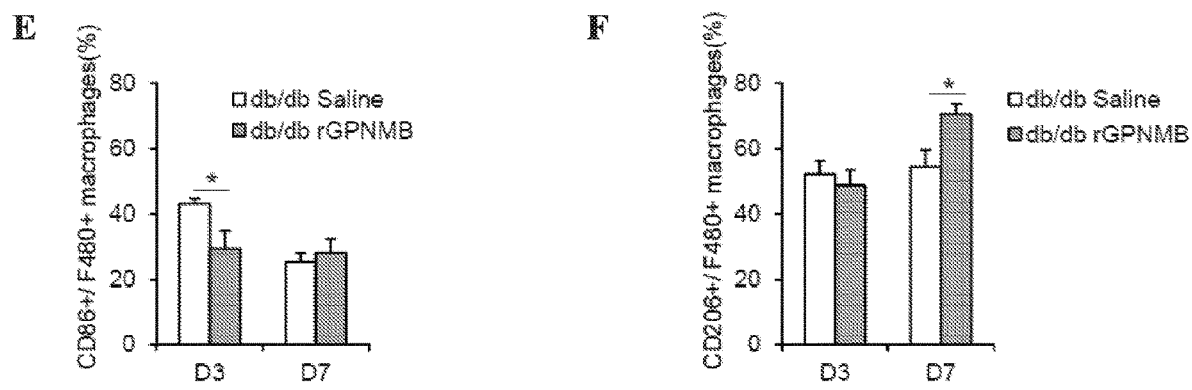

Diabetic Wounds Are Associated With Diminished Expression of GPNMB, Attenuated Recruitment of MSCs, and Delayed Wound Healing Type 2 diabetes has shown to impair the recruitment of stem and progenitor cells to the site of injury and delay wound healing (Fiorina et al., 2010). By observing the functional role of GPNMB in promoting the recruitment of MSCs in normal acute wounds, we next sought to determine whether diminished MSC recruitment and delayed wound healing in diabetic wounds are associated with impaired GPNMB signaling following skin wounding. For this, wounded skins were harvested from non-diabetic (db/+) and diabetic (db/db) mice and the expression level of Gpnmb mRNA was compared. Wounds of db/db mice exhibited a significantly attenuated expression of Gpnmb mRNA by 4-fold at day 3 post-wounding, compared to non-diabetic control mice (FIG. 10A). This response was associated with delayed wound closure in db/db mice (FIGS. 10B-C) and attenuated number of MSCs in the wound of db/db mice by 3-fold (day 7), compared to non-diabetic mice (FIG. 10D).

Figure 11:
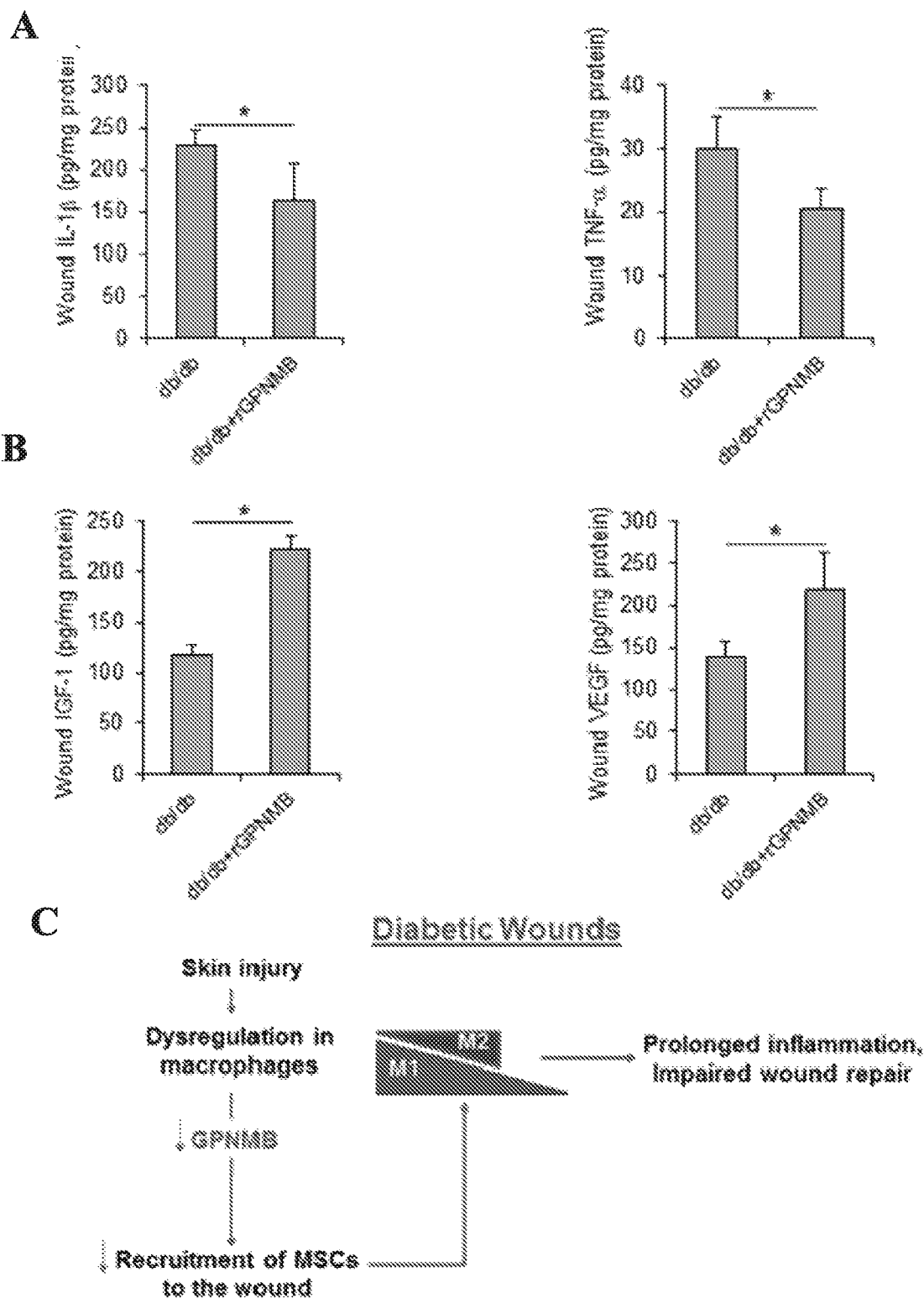
FIGS. 11A-C show the levels of wound pro-inflammation cytokines IL-1β and TNF-α (FIG. 11A) and pro-healing factors IGF-1 and VEGF (FIG. 11B) by ELISA at day 14 post-wounding in db/db mice with or without rGPNMB treatment. Data are presented as mean±SEM. n=6, $*p<0.05$.

Topical Treatment of rGPNMB Restores MSC Recruitment, Increases the Trafficking of M2 Macrophage, and Accelerates Wound Closure in Diabetic Wounds Since diabetic wound environment attenuated the expression of GPNMB and the recruitment of MSCs following skin wounding, we next sought to determine whether supplementing the availability of GPNMB in the wound can reverse the MSC response and promote wound repair in diabetic wounds. Indeed, the topical treatment of rGPNMB to the wounds of db/db mice could accelerate wound closure (FIGS. 10B-C) and increase the number of MSCs in the wound by 2-fold at day 3 (FIG. 10D), which were associated with significantly diminished expression of pro-inflammatory cytokines IL-1β and TNF-α (FIG. 11A) and upregulated expression of pro-healing factors VEGF and IGF-1 in the wound (FIG. 11B). Finally, flow cytometric phenotyping of wound-isolated macrophage revealed that the topical application of rGPNMB increased the trafficking of M2 macrophages while attenuating M1 macrophages in wounds of db/db mice (FIGS. 10E-F). Collectively, our results supports that GPNMB activity is dysregulated in diabetic wound environment and this may contribute to the impaired MSC recruitment and delayed wound healing (FIG. 11C).

The complete disclosure of all patents, patent applications, and publications, and electronically available materials cited herein are incorporated by reference. Any disagreement between material incorporated by reference and the specification is resolved in favor of the specification. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

REFERENCES

Fiorina P, Pietramaggiori G, Scherer S S, Jurewicz M, Mathews J C, Vergani A, et al. (2010) The mobilization and effect of endogenous bone marrow progenitor cells in diabetic wound healing. *Cell Transplant* 19:1369-81.

Gabriel T L, Tol M J, Ottenhof R, van Roomen C, Aten J, Claessen N, et al. (2014) Lysosomal stress in obese adipose tissue macrophages contributes to MITF-dependent Gpnmb induction. *Diabetes* 63:3310-23.

Halfon S, Abramov N, Grinblat B, Ginis I (2011) Markers distinguishing mesenchymal stem cells from fibroblasts are downregulated with passaging. *Stem Cells Dev* 20:53-66.

Katayama A, Nakatsuka A, Eguchi J, Murakami K, Teshigawara S, Kanzaki M, et al. (2015) Beneficial impact of Gpnmb and its significance as a biomarker in nonalcoholic steatohepatitis. *Sci Rep* 5:16920.

Li B, Castano A P, Hudson T E, Nowlin B T, Lin S L, Bonventre J V, et al. (2010) The melanoma-associated transmembrane glycoprotein Gpnmb controls trafficking of cellular debris for degradation and is essential for tissue repair. *FASEB J* 24:4767-81.

Mandavian Delavary B, van der Veer W M, van Egmond M, Niessen F B, Beelen R H (2011) Macrophages in skin injury and repair. *Immunobiology* 216:753-62.

Tang Y, Wu X, Lei W, Pang L, Wan C, Shi Z, et al. (2009) TGF-beta1-induced migration of bone mesenchymal stem cells couples bone resorption with formation. *Nat Med* 15:757-65.

Witte M B, Barbul A (1997) General principles of wound healing. *Surg Clin North Am* 77:509-28.

Yu B, Sondag G R, Malcuit C, Kim M H, Safadi F F (2016) Macrophage-Associated Osteoactivin/GPNMB Mediates Mesenchymal Stem Cell Survival, Proliferation, and Migration Via a CD44-Dependent Mechanism. *J Cell Biochem* 117:1511-21.

What is claimed is:

1. A method for accelerating the healing of a skin wound of a subject in need thereof, the method comprising contacting the skin wound with a wound healing composition comprising the soluble form of the extracellular fragment of glycoprotein nonmelanoma clone B (GPNMB) protein, whereby the wound healing composition is contacted with the skin wound in an amount effective to recruit and increase the number of mesenchymal stem cells in the skin wound and thereby accelerate healing of the skin wound.

2. The method of claim 1, wherein the subject has impaired healing capabilities.

3. The method of claim 1, wherein the subject is diabetic or is elderly.

4. The method of claim 1, wherein the skin wound is a chronic wound.

5. The method of claim 1, wherein the skin wound is a pressure sore.

6. The method of claim 1, wherein the wound healing composition further comprises a pharmaceutically acceptable carrier.

7. The method of claim 6, wherein the wound healing composition is a topical formulation.

8. The method of claim 1, wherein the wound healing composition is a sustained release composition.

9. The method of claim 1, wherein the wound healing composition is associated with a biocompatible material.

10. The method of claim 9, wherein the biocompatible material is a tissue scaffold.

11. The method of claim 10, wherein the tissue scaffold comprises a biocompatible material selected from the group consisting of an allograft, a xenograft, a collagen, and a gelatin.

12. The method of claim 9, wherein the biocompatible material is a polymer.

13. The method of claim 12, wherein the polymer is a biodegradable polymer.

14. The method of claim 1, wherein the skin wound is selected from the group consisting of a thermic wound, a chemical wound, an incised wound, a stab wound, a laceration, a puncture wound, an abrasion, a graze, a burn, frostbite, or a bite wound.

15. The method of claim 1, wherein the soluble form of the extracellular fragment of the GPNMB protein is a recombinant human soluble form.

* * * * *

UNITED STATES PATENT AND TRADEMARK OFFICE
CERTIFICATE OF CORRECTION

| | | |
|---|---|---|
| PATENT NO. | : 11,554,158 B2 | Page 1 of 1 |
| APPLICATION NO. | : 16/093270 | |
| DATED | : January 17, 2023 | |
| INVENTOR(S) | : Kim et al. | |

It is certified that error appears in the above-identified patent and that said Letters Patent is hereby corrected as shown below:

In the Specification

Column 1, before the subtitle SEQUENCE LISTING, insert the following paragraph:
-- GOVERNMENT FUNDING
This invention was made with government support under the grant(s) AR048892 awarded by the National Institutes of Health. The government has certain rights in the invention. --

Signed and Sealed this
Twenty-second Day of April, 2025

Coke Morgan Stewart
*Acting Director of the United States Patent and Trademark Office*